US011369318B2

(12) United States Patent
Sarkaria et al.

(10) Patent No.: US 11,369,318 B2
(45) Date of Patent: Jun. 28, 2022

(54) IMAGE PROCESSING OF STREPTOCOCCAL INFECTION IN PHARYNGITIS SUBJECTS

(71) Applicant: Light AI Inc., Vancouver (CA)

(72) Inventors: Sarbjit Sarkaria, Richmond (CA); Steven Rebiffe, Richmond (CA); Udit Gupta, Vancouver (CA); Mahendran Maliapen, Vancouver (CA); Peter Whitehead, West Vancouver (CA)

(73) Assignee: Light AI, Inc., Vancouver (CA)

( * ) Notice: Subject to any disclaimer, the term of this patent is extended or adjusted under 35 U.S.C. 154(b) by 161 days.

(21) Appl. No.: 16/589,077

(22) Filed: Sep. 30, 2019

(65) Prior Publication Data

US 2020/0107787 A1   Apr. 9, 2020

Related U.S. Application Data

(60) Provisional application No. 62/855,875, filed on May 31, 2019, provisional application No. 62/743,245, filed on Oct. 9, 2019.

(51) Int. Cl.
*A61B 5/00* (2006.01)
*A61K 9/00* (2006.01)
(Continued)

(52) U.S. Cl.
CPC .......... *A61B 5/7267* (2013.01); *A61K 9/0053* (2013.01); *G06K 9/6256* (2013.01);
(Continued)

(58) Field of Classification Search
CPC ........ G16H 50/20; G16H 50/30; G16H 50/50; G16H 50/70; G16H 10/60; G16H 40/67;
(Continued)

(56) References Cited

U.S. PATENT DOCUMENTS

2012/0209093 A1*  8/2012 Olszewski ........... A61B 6/5217
                                                                 600/407
2017/0156597 A1    6/2017 Whitehead
                          (Continued)

FOREIGN PATENT DOCUMENTS

CN         106295139 A     1/2017
WO   WO 2017/214061 A1    12/2017

OTHER PUBLICATIONS

Askarian, B. et al., "Novel Image Processing Method for Detecting Strep Throat (Streptococcal Pharyngitis) Using Smartphone," Sensors, vol. 19, Jul. 27, 2019, pp. 1-17.
(Continued)

*Primary Examiner* — Ajibola A Akinyemi
(74) *Attorney, Agent, or Firm* — Fenwick & West LLP

(57) ABSTRACT

A method for determining a disease state prediction, relating to a potential disease or medical condition of a subject, includes accessing a set of subject images, the subject images capturing a part of a subject's body, and accessing a set of clinical factors from the subject. The clinical factors are collected by a device or a medical practitioner substantially contemporaneously with the capture of the subject images. The subject images are inputted into an image model to generate disease metrics for disease prediction for the subject. The disease metrics generated by the image model and the clinical factors are inputted into a classifier to determine the disease state prediction, and the disease state prediction is returned.

27 Claims, 11 Drawing Sheets

Detection System
100

(51) Int. Cl.
   *G16H 30/40* (2018.01)
   *G06K 9/62* (2022.01)
   *G16H 50/50* (2018.01)
   *A61K 39/09* (2006.01)
(52) U.S. Cl.
   CPC .............. *G16H 30/40* (2018.01); *G16H 50/50* (2018.01); *A61K 39/092* (2013.01)
(58) Field of Classification Search
   CPC ........ G16H 40/63; G16H 30/20; G16H 70/60; G16H 30/40; G16H 15/00; G16H 80/00; G16H 10/20; G16H 20/10; G16H 20/17; G16H 20/30; G16H 20/40; G16H 20/60; G16H 20/70; G16H 30/00
   USPC ......................................................... 455/128
   See application file for complete search history.

(56) References Cited

U.S. PATENT DOCUMENTS

| | | | |
|---|---|---|---|
| 2018/0001184 A1 | 1/2018 | Tran et al. | |
| 2018/0045798 A1 | 2/2018 | Yokosawa et al. | |
| 2018/0160887 A1* | 6/2018 | Hefez | A61B 1/000094 |
| 2018/0242848 A1* | 8/2018 | Dacosta | A61B 5/742 |
| 2019/0110753 A1 | 4/2019 | Zhang et al. | |
| 2019/0171906 A1* | 6/2019 | Sodhani | G06K 9/623 |

OTHER PUBLICATIONS

Centers for Disease Control and Prevention, "Ambulatory Care Use and Physician office visits," last reviewed Jan. 19, 2017, two pages, [Online] [Retrieved on Dec. 5, 2019] Retrieved from the Internet <URL: https://www.cdc.gov/nchs/fastats/physician-visits.htm>.
Colletti, T. et al., "Strep throat: guidelines for diagnosis and treatment," JAAPA, vol. 18, No. 9, Sep. 2005, pp. 38-44.
Gonzales, R. et al., "Antibiotic Prescribing for Adults with Colds, Upper Respiratory Tract Infections, and Bronchitis by Ambulatory Care Physicians," JAMA, vol. 278, No. 11, Sep. 17, 1997, pp. 901-904.
Lane, P. M. et al., "Simple Device for the direct visualization of oral-cavity tissue fluorescence," Journal of Biomedical Optics, vol. 11, No. 2, Mar.-Apr. 2006, pp. 1-7.
Laronde, D. M. et al., "A Magic Wand for the Community Dental Office? Observations from the British Columbia Oral Cancer Prevention Program," Journal of the Canadian Dental Association, vol. 73, No. 7, Sep. 2007, pp. 607-609.
Linder, J.A. et al., "Antibiotic treatment of Children with Sore Throat," JAMA, vol. 294, No. 18, Nov. 9, 2005, pp. 2315-2322.
Litjens, G. et al., "A Survey on Deep Learning in Medical Image Analysis," arXiv: 1702.05747, Jun. 4, 2017, pp. 1-38.
McIsaac, W.J. et al., "Empirical Validation of Guidelines for the Management of Pharyngitis in Children and Adults," JAMA, vol. 291, No. 13, Apr. 7, 2004, pp. 1587-1595.
Nyquist, A. C. et al., "Antibiotic Prescribing for Children with Colds, Upper Respiratory Tract Infections, and Bronchitis," JAMA, vol. 279, No. 11, Mar. 18, 1998, pp. 875-877.
Poh, C. F. et al., "Direct Fluorescence Visualization of Clinically Occult High-risk Oral Premalignant Disease Using a Simple Handheld Device," Head & Neck, vol. 29, No. 1, Jan. 2007, pp. 71-76.
Poh, C. F. et al., "Fluorescence Visualization Detection of Field Alterations in Tumor Margins of Oral Cancer Patients," Clinical Cancer Research, vol. 12, No. 22, Nov. 15, 2006pp. 6716-6722.
Roos, R., "Study: Antibiotic overuse still the rule for sore throat, bronchitis," Oct. 3, 2013, pp. 1-3, [Online] [Retrieved on Dec. 5, 2019] Retrieved from the Internet <URL: http://www.cidrap.umn.edu/news-perspective/2013/10/study-antibiotic-overuse-still-rule-sore-throat-bronchitis>.
Salkind, A.R. et al., "Economic Burden of Adult Pharyngitis: The Payer's Perspective," Value in Health, vol. 11, Nov. 4, 2008, pp. 621-627.
Shichijo, A. et al., "Application of Convolutional Neural Networks in the Diagnosis of Helicobacter pylori Infection Based on Endoscopic Images," EBioMedicine, vol. 25, Oct. 16, 2017, pp. 106-111.
Shulman, S.T. et al., "Clinical Practice Guideline for the Diagnosis and Management of Group A Streptococcal Pharyngitis: 2012 Update by the Infectious Diseases Society of America," Clinical Infectious Diseases, vol. 55, Issue 10, Nov. 15, 2012, pp. e86-e102.
PCT International Search Report and Written Opinion. PCT Application No. PCT/CA2019/051401, dated Dec. 13, 2019, 15 pages.

* cited by examiner

IMAGE PROCESSING OF STREPTOCOCCAL INFECTION IN PHARYNGITIS SUBJECTS

CROSS-REFERENCE TO RELATED PATENT APPLICATION

This patent application claims priority to U.S. Provisional Patent Application No. 62/743,245, filed on Oct. 9, 2018, and to U.S. Provisional Patent Application No. 62/855,875, filed on May 31, 2019, which are incorporated herein in their entirety.

BACKGROUND

Field of Art

The disclosure relates to image processing and particularly to using images captured of a subject's throat to evaluate for the presence of disease without culturing.

Description of the Related Art

Sore throats account for around 1% of all primary care visits in North America. All too often the cause of the complaint is viral not bacterial. However, a rapid and accurate diagnosis is challenging for medical practitioners and it is all too easy to adopt a bias towards prescribing antibiotics, thereby contributing to their over-use. This is problematic because it often results in unnecessary spending on medication, as well as contributing to a general increase in antibiotic resistance. Clinical tests, which traditionally involve culturing in vitro for presence of bacteria can be slow, taking up to 72 hours to offer results, are difficult to administer properly, especially in children, and as such can be inaccurate. There is a clear need for a more reliable, fast and automatic detection process.

SUMMARY

A detection system determines disease state predictions, relating to a potential disease and/or medical condition of a subject (also referred to herein as a "patient"), using a chained model. The chained model includes an image model and a classifier, according to some embodiments. The chained model accesses a set of subject images, the subject images capturing a part of a subject's body, and a set of clinical factors from the subject. The clinical factors are collected by a device or a medical practitioner substantially contemporaneously with the capture of the subject images. According to some embodiments, the clinical factors may include relevant information for diagnosing the subject with the respective potential disease and/or medical condition. The subject images are inputted into an image model to generate disease metrics for disease prediction for the subject. The image model may be trained using a set of training images and a set of training labels associated with a first set of training subjects, according to some embodiments. For example, the training labels may include a label indicating a presence of a pathogen in the subject associated with the respective training image.

The disease metrics generated by the image model and the clinical factors for the subject together are inputted into a classifier to determine the disease state prediction, and the disease state prediction is returned by the chained model. The classifier may be trained using a set of training labels, a set of training disease metrics, and a set of training clinical factors associated with a second set of training subjects, according to some embodiments. In some embodiments, the second set of training subjects, may be different than the first set of training subjects. The set of training disease metrics may be generated by inputting a set of training subject images associated with the second set of training subjects to the trained image model. Using the chained model, the detection system may provide for dry in-situ clinical prediction related to the potential disease and/or medical condition (e.g., the presence/absence of bacterial and viral pathogen infections) without the need for any pathological or laboratory tests, according to some embodiments.

DETAILED DESCRIPTION

I. System Architecture

Figure 1:
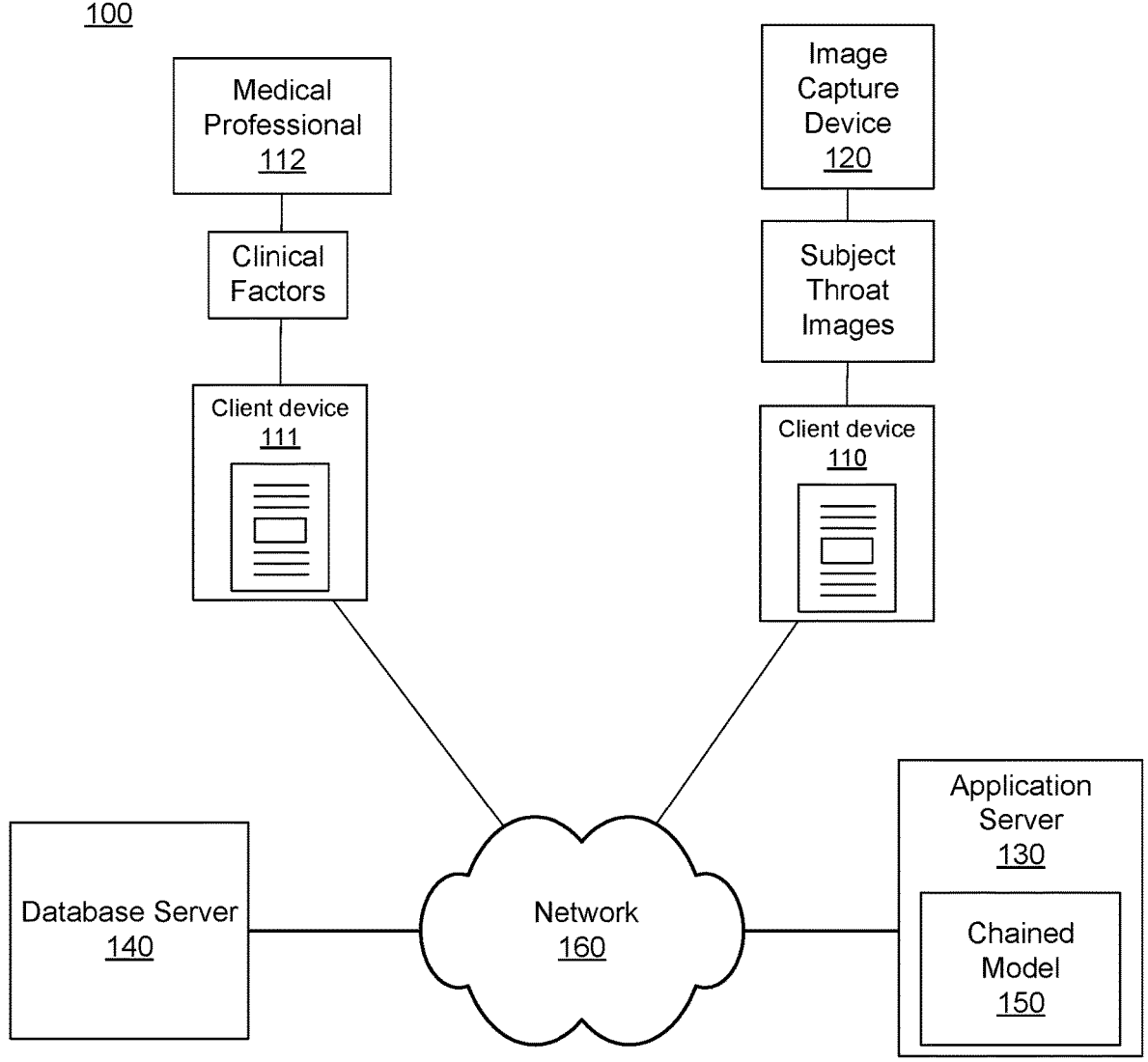
FIG. 1 shows a detection system for analyzing a combination of images of a subject's throat and subject-associated clinical factors to determine a disease state prediction for the subject, according to one embodiment.

FIG. 1 shows a detection system for analyzing a combination of images of the inside of a subject's throat and subject-associated clinical factors to determine a disease state prediction for the subject (also referred to herein as the "patient"), according to one embodiment. A disease state prediction is related to a disease or medical condition the subject may potentially have. For example, the disease state prediction may indicate a presence or probability of the subject having a streptococcal infection. The detection system analyzes images provided by an image capture device 120 and clinical factors provided by a medical professional 112 or device to determine a disease state related to a type of infection present in the subject. In some embodiments, the detection system 100 is used for detecting streptococcal infections in subjects experiencing pharyngitis. In other embodiments the detection system 100 is used for detecting other diseases and conditions.

The detection system 100 includes client computing devices 110, 111, an image capture device 120, an application server 130, also referred to herein as server 130, database server 140, and a chained model 150. Although FIG. 1 illustrates only a single instance of most of the components of the detection system 100, in practice more than one of each component may be present, and additional or fewer components may be used. In one embodiment, the chained model 150 is a part of the client device 110, and functions of the chained model 150 are performed locally on the client device 110.

I.A. Client Device and Application

The client devices 110, 111 interact with the detection system 100 via a network 160. In one embodiment, the network 160, system 100, client devices 110, 111, and/or server 130 are a secure network handling sensitive or confidential information, for example they may be designed to provide for restricted data access, encryption of data, and otherwise may be compliant with medical information protection regulations such as HIPAA. For purposes of explanation and clarity it is useful to identify at least two different types of users. One type of user is a subject who potentially has pharyngitis or another throat related disease and makes use of the system 100 at least in part to obtain a disease state prediction provided by the server 130. As will be explained below, a set of subject throat images of the subject's throat collected by an image capture device 120 are provided to a client device 110, which in turn reports to the application server 130, which in turn can initiate a process to determine a disease state prediction which is provided to the user through the client device 110.

Another type of user is a medical professional 112 who provides clinical factors collected by a device or a medical practitioner substantially contemporaneously with the capture of the set of subject throat images to a client device 111 (which may also be the same as client device 110), which in turn reports to the application server 130, which in turn can be combined with the subject throat images to initiate a process to determine a disease state prediction which is provided to the user through the client device 110. The medical professional 112 may operate the image capture device 120 and client device 110. Alternatively, the subject may instead operate the image capture device 120 and the client device 110.

The client device 110, 111 is a computer system. An example physical implementation is described more completely below with respect to FIG. 2. The client device 110, 111 is configured to communicate (e.g., wirelessly or via a wired link) with the detection system 100 via network 160. With network 160 access, the client device 110 transmits to the detection system 100 the set of subject throat images captured by the image capture device 120, and the client device 111 transmits to the detection system 100 the clinical factors provided by the medical professional 112.

In addition to communicating with the application server 130, client devices 110, 111 connected to the detection system 100 may also exchange information with other connected client devices 110, 111.

The client device 110 may also perform some data and image processing on the set of subject throat images locally using the resources of client device 110 before sending the processed data through the network 160. The client device 111 may also perform some data processing on the clinical factors locally using the resources of client device 111 before sending the processed data through the network 160. Images and clinical factors sent through the network 160 are received by the application server 130 where they are analyzed and processed for storage and retrieval in conjunction with database server 140. The application server 130 may direct retrieval and storage request to the database system 130 as required by the client devices 110, 111.

The client devices 110 may communicate with the image capture device 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. In other implementations, other types of wireless connections are used (e.g., infrared, cellular, 4G, 5G, 802.11).

Although client devices 110 and image capture devices 120 are described above as being separate physical devices (such as a computing device and an image sensor, respectively), in an embodiment, the image capture device 120 may include aspects of the client device 110. For example, an image capture device may include an audiovisual interface including a display or other lighting elements as well as speakers for presenting audible information. In such an implementation the image capture device 120 itself may present the contents of information obtained from server 130, such as the disease state prediction determined by the detection system 100, provided by the server 130 directly, in place of or in addition to presenting them through the client devices 110.

In one embodiment, the client device 110 may be a smartphone, and part of the image capture device 120 may be a smartphone attachment. In such an implementation, a built-in camera of the smart phone combined with optical elements of the smartphone attachment provide the functionality of the image capture device 120.

In one embodiment, one client device may act as both the client device 110 and the client device 111.

I.B. Application Server

Figure 2:
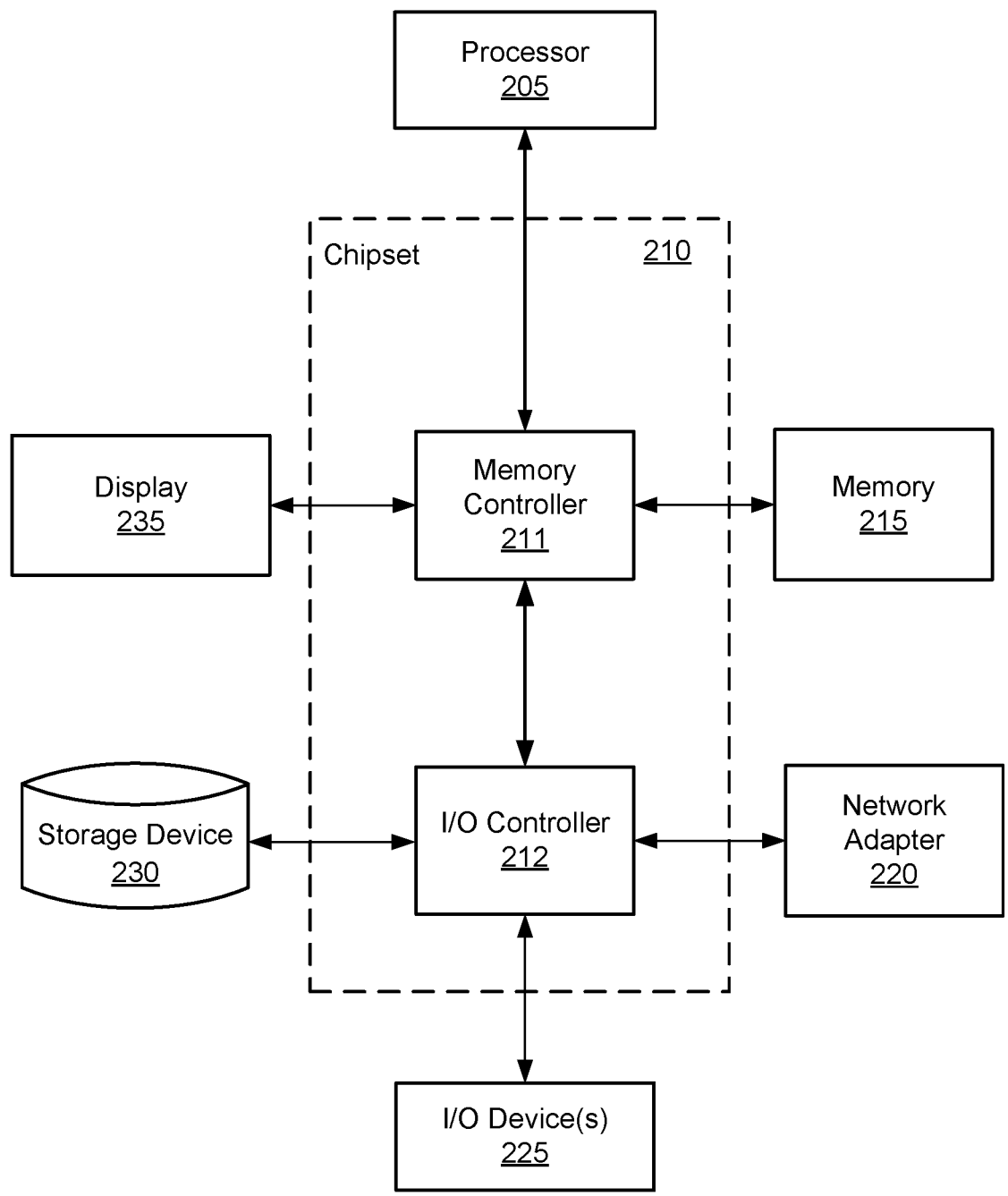
FIG. 2 is a high-level block diagram illustrating an example of a computing device used either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access to and use of detection system 100 by many different client devices 110, 111 through network 160, and thus at a high level can be generally characterized as a cloud-based system. The application server 130 generally provides a platform for subjects and medical professionals 112 to report data recorded by the client devices 110, 111 associated with the subject's pharyngitis, collaborate on treatment plans, browse and obtain information relating to their condition, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a subject by subject basis. Towards this end, the application server 130 creates a subject profile for each user. The subject profile is a set of data that characterizes a subject 113 of the detection system 100. The subject profile may include identify information about the subject such as age, gender, a subject's relevant medical history, and a list of non-subject users authorized to access the subject profile. The profile may further specify a device identifier, such as a unique media access control (MAC) address identifying the one or more client devices 110, 111 or image capture devices 120 authorized to submit data (such as a set of subject throat images) for the subject.

The application server 130 also creates profiles for health care providers 112. A health care provider profile may include identifying information about the health care provider 112, such as the office location, qualifications and certifications, and so on. The health care provider profile also includes information about their subject population. The provider profile may include access to all of the profiles of that provider's subjects, as well as derived data from those profiles such as aggregate demographic information. This data may be further subdivided according to any type of data stored in the subject profiles, such as by geographic area (e.g., neighborhood, city) over by time period (e.g., weekly, monthly, yearly).

The application server 130 receives client factors and subject throat images from the client devices 110, 111 triggering a variety of routines on the application server 130. In the example implementations described below, the chained model 150 executes routines to access subject throat images as well as clinical factors, analyze the images and data, and output the results of its analysis to subjects or medical professionals 112.

I.C. Database Server

The database server 140 stores subject and healthcare provider related data such as profiles, medication events, subject medical history (e.g., electronic medical records). Subject and provider data is encrypted for security and is at least password protected and otherwise secured to meet all Health Insurance Portability and Accountability Act (HIPAA) requirements. Any analyses that incorporate data from multiple subjects and are provided to users is de-identified so that personally identifying information is removed to protect subject privacy.

Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

Figure 4:
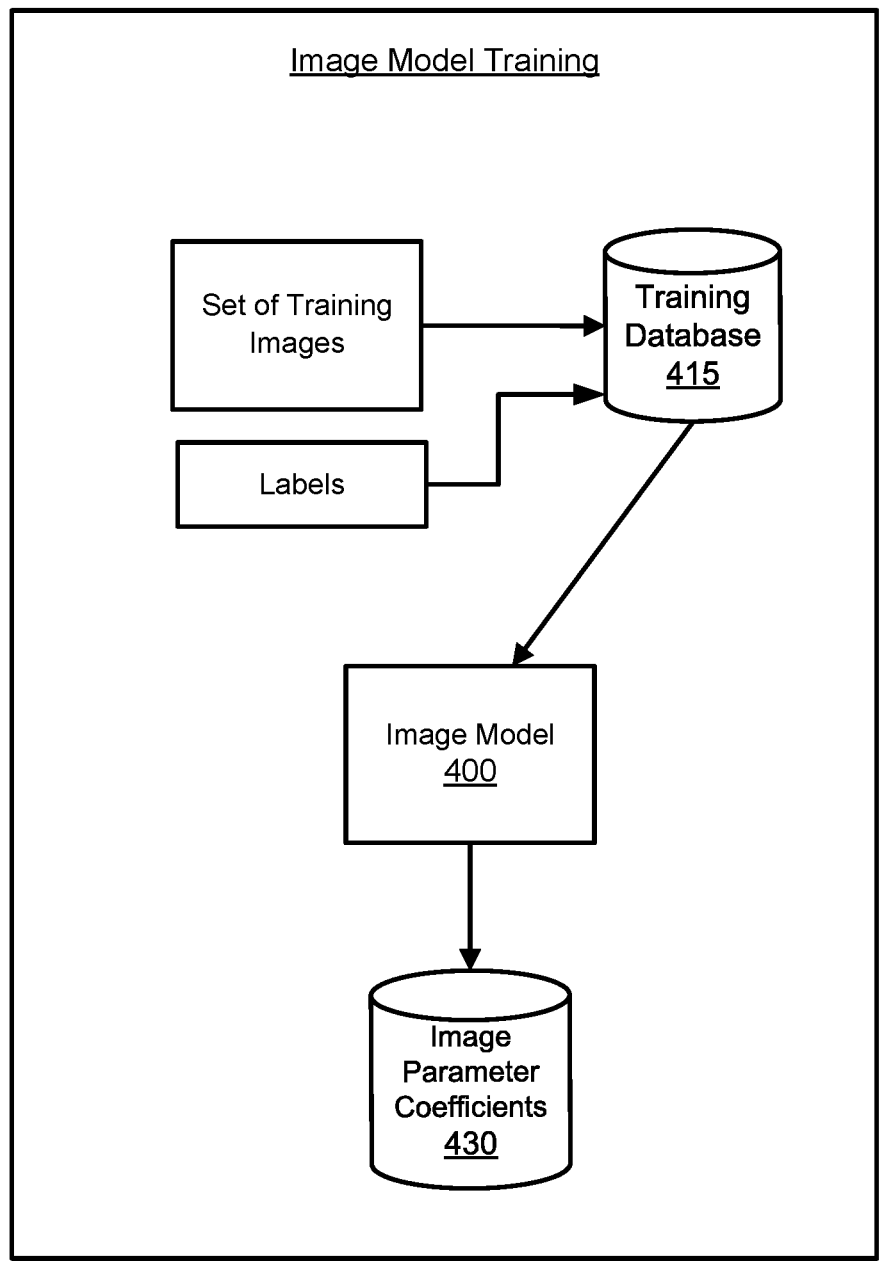
FIG. 4 illustrates a process for training of an image model within a chained model, according to one embodiment.
Figure 5:
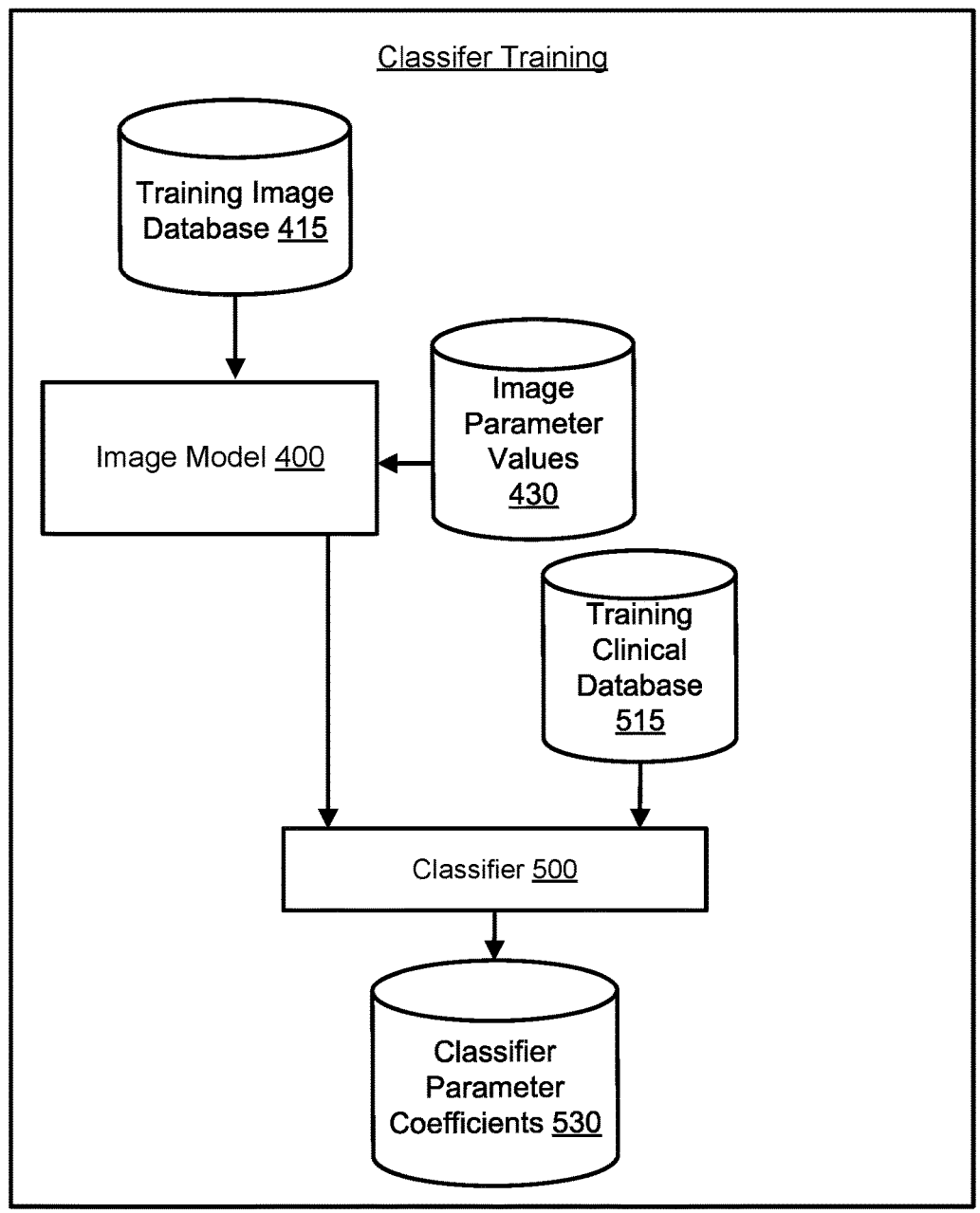
FIG. 5 illustrates a process for training of a classifier within a chained model, according to one embodiment.
Figure 6:
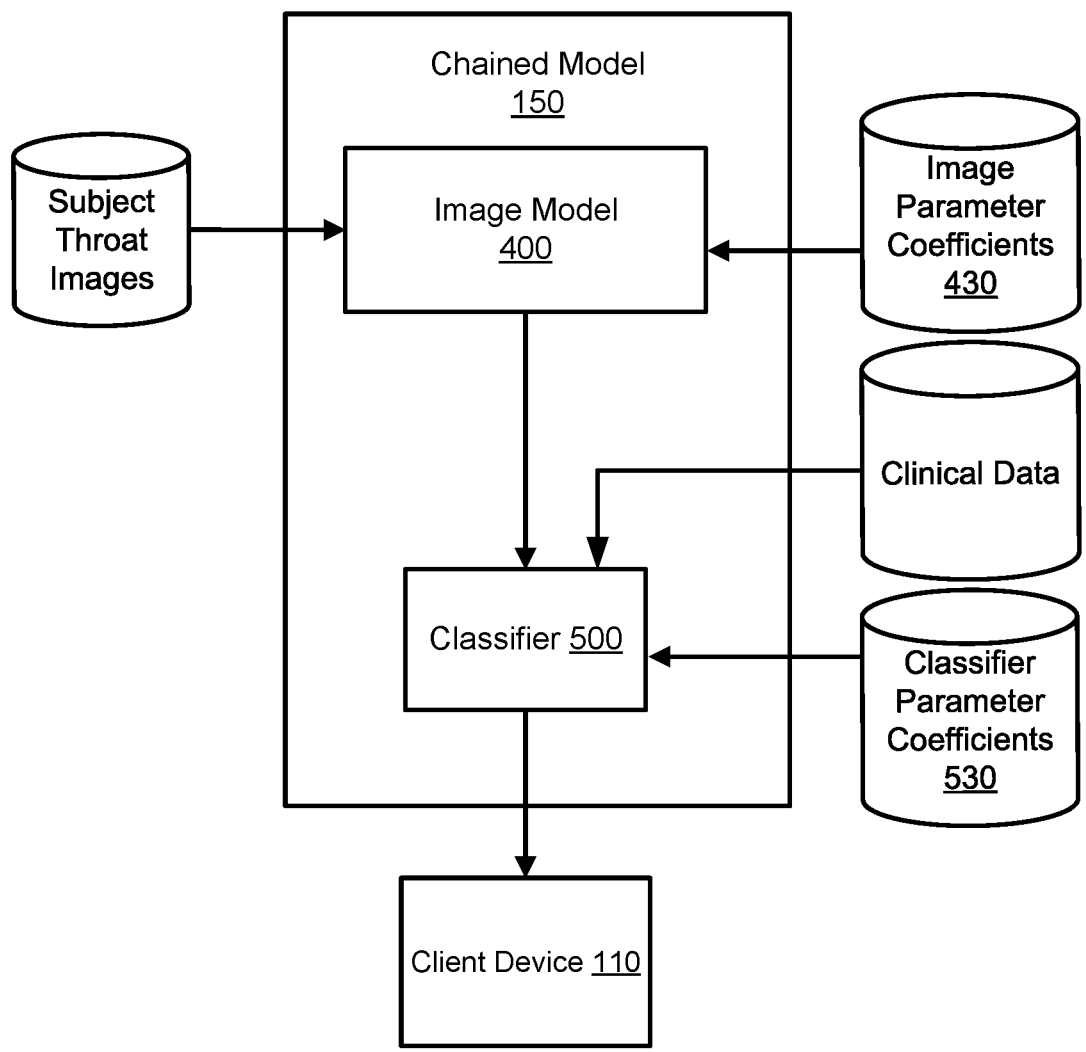
FIG. 6 illustrates a process for generating disease state predictions using a chained model, according to one embodiment.

With respect to the descriptions of FIGS. 4-6, the contents of the databases described with respect to those figures may be stored in databases physically proximate to the application server 130 and separate from database server 140 as illustrated.

I.D. Network

The network 160 represents the various wired and wireless communication pathways between the client devices 110, 111, the image capture device 120, the application server 130, and the database server 140. Network 160 uses standard Internet communications technologies and/or protocols. Thus, the network 160 can include links using technologies such as Ethernet, IEEE 802.11, integrated services digital network (ISDN), asynchronous transfer mode (ATM), etc. Similarly, the networking protocols used on the network 160 can include the transmission control protocol/Internet protocol (TCP/IP), the hypertext transport protocol (HTTP), the simple mail transfer protocol (SMTP), the file transfer protocol (FTP), etc. The data exchanged over the network 160 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, 111, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 160.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110, 111 will vary in size, power requirements, and performance from those used in the application server 130 and the database server 140. For example, client devices 110, 111 which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the analyses introduced above. In one embodiment, the processing power of the application server 130 provided by a service such as Amazon Web Services™ or Microsoft Azure™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Image Capture and Clinical Factors

III.A. Image Capture Device

Figure 3C:
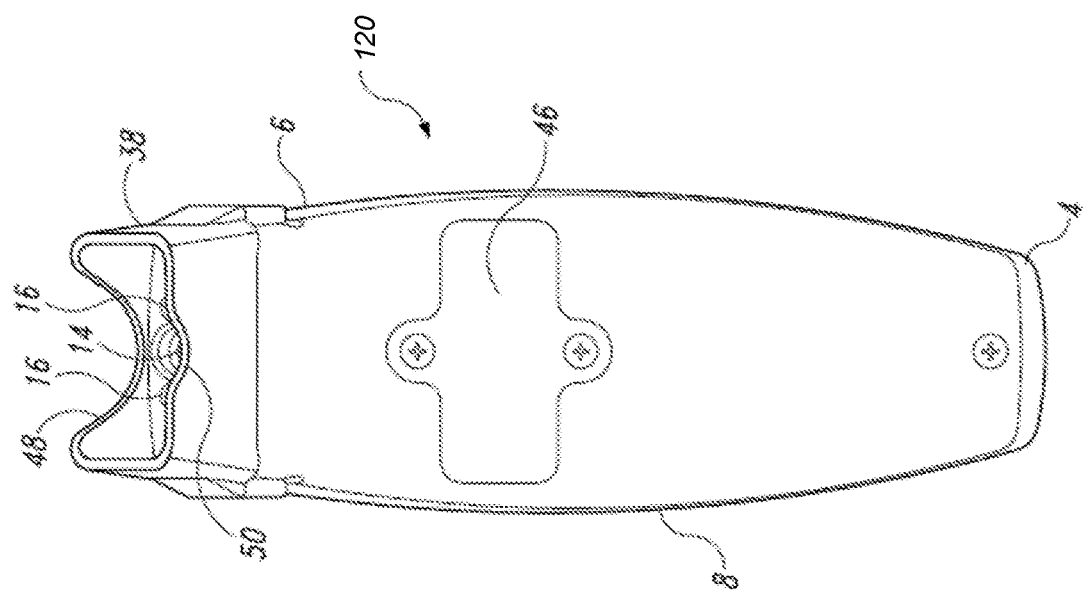
FIGS. 3A-3I depicts various views of an image capture device, according to one embodiment.
Figure 3B:
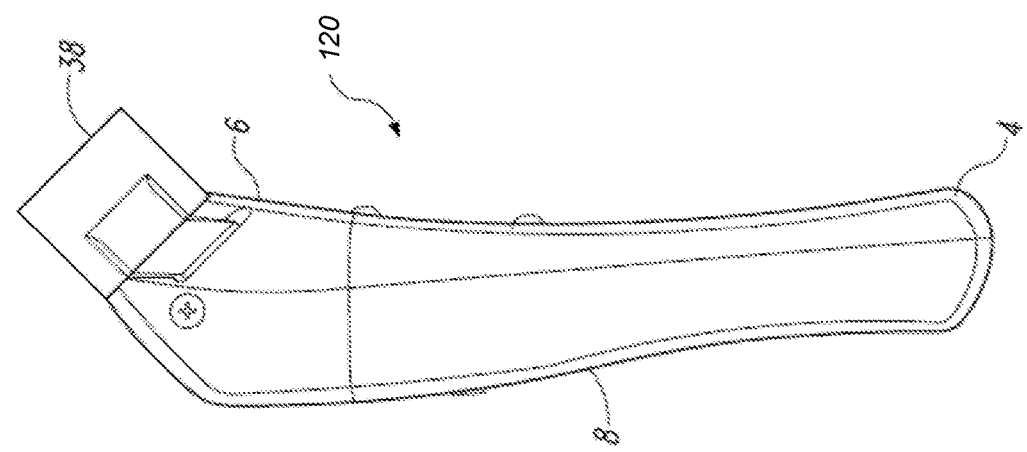
Figure 3A:
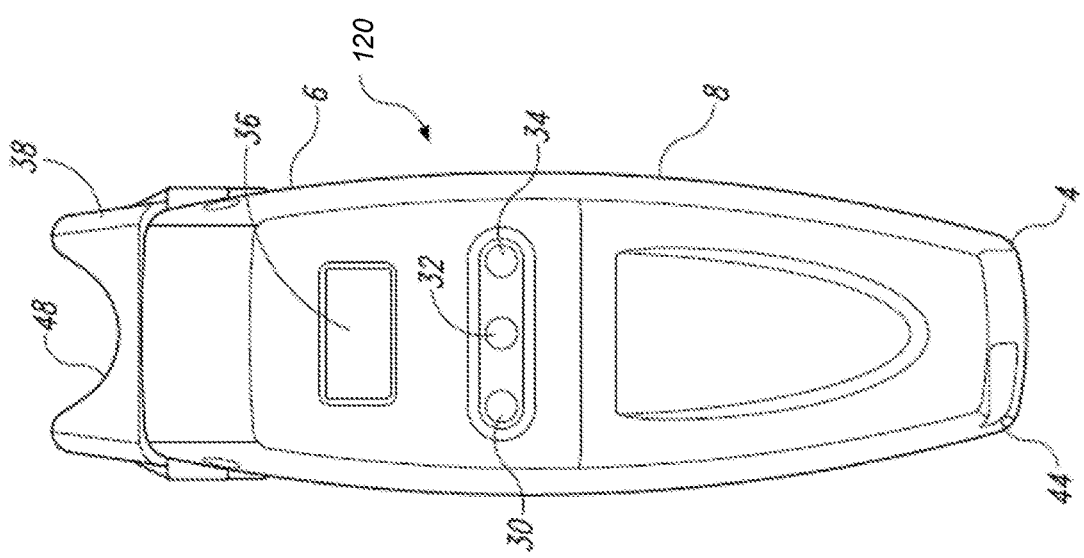

FIGS. 3A-3C depict three views of an exemplary image capture device 120, according to one embodiment. The embodiment depicted is configured for use in a human oral cavity (mouth and if desired upper throat). In other embodiments, the image capture device is configured to capture images of other parts of the body or other objects. For example, in one embodiment, the image capture device 120 is configured to capture images of a subject's skin. The scanning and detection device can be any desired shape suitable for a given target site, for example a catheter or endoscope or other configuration (e.g., colposcope, laparascope, etc.) shaped to be inserted into or otherwise introduced into or aimed toward the body of a subject.

In one embodiment, the image capture device 120 comprises a proximal end 4 and a distal end 6, with the distal end 6 configured to introduce into or aim towards an in vivo biological target site suspected of having an infection. Image capture device 120 comprises housing 8 having an excitation light emitter 10 at the distal end 6, the excitation light emitter 10 configured to emit excitation light selected to elicit fluorescent light from the suspected infection at the target site; if desired, multiple excitation light emitters can be provided, each for a different wavelength/wavelength band of excitation light. The image capture device 120 may further comprise a light sensor as well as a heat sensor 14 (refer, e.g., to FIGS. 3D and 3F). The light sensor is configured to detect at least fluorescent light emanating from the target site, and heat sensor 14 is configured to at least detect and identify heat levels above ambient body temperature emanating from the infection at the target site.

In one embodiment, the detection system further comprises operably connected computer-implemented programming configured to accept fluorescent light data associated with the fluorescent light and thermal data associated with the heat levels above ambient body temperature and interpret the data to determine a probability whether the target site contains an infection. Such computer-implemented programming can be contained within housing 8 or can be located externally.

Image capture device 120 also contains three buttons for user interaction. The first control button 30 controls the illumination LED (white light emitter). The second button 32 initiates an image/scan acquisition procedure such as a fluorescent image/sensing procedure. The third control button 34 initiates a temperature acquisition procedure. Other or fewer buttons can also be provided as desired.

Figure 3D:
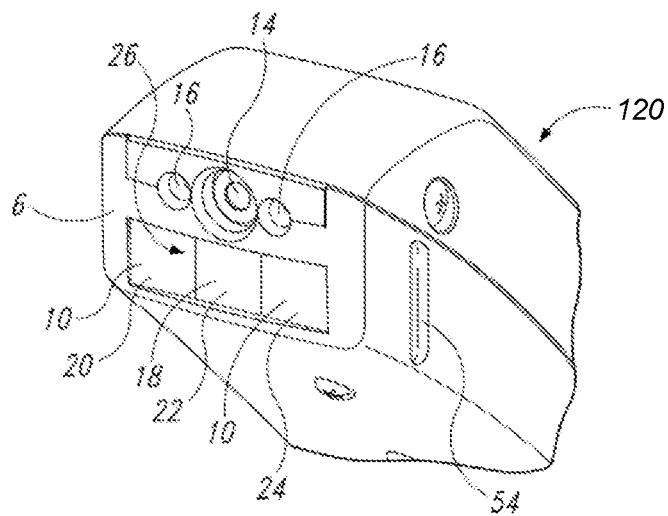
Figure 3E:
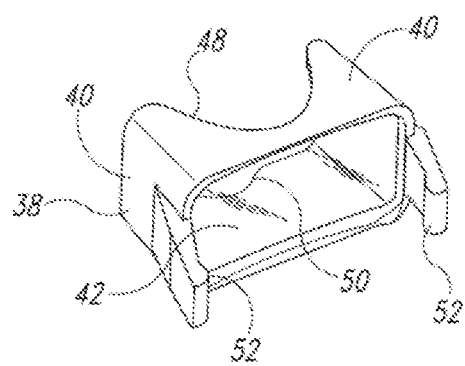
Figure 3F:
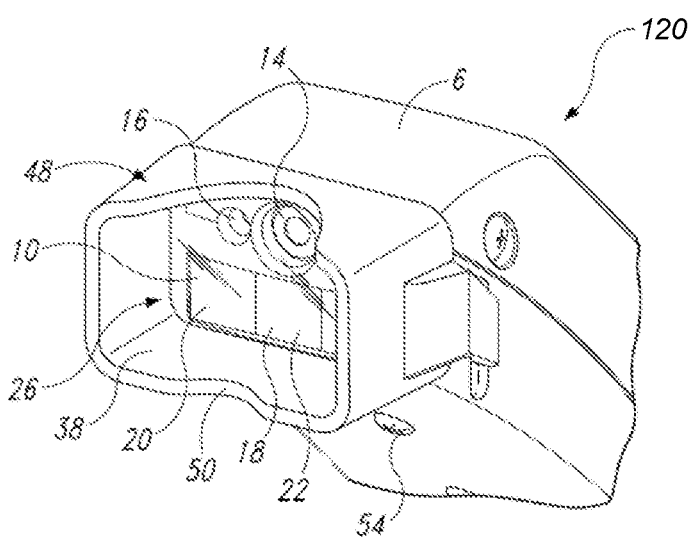

As shown in FIG. 3D and FIG. 3F, image capture device 120 can comprise an illumination light emitter 16 and an imaging system 26 comprising a camera 18. One or more filters configured to transmit only desirable wavelengths/indicators of light or heat can also be provided, such as first emanating light filter 20, emanating heat filter 22, and second emanating light filter 24.

Image capture device 120 further contains a display screen 36, which can display spectrographic results, images of the target site, diagnostic results, false-color representations of the data received from the target site, and the like. The display can also convey other information if desired, such as date, time, subject name, etc. Also shown is an easily removable separable distal element 38 sized and configured to removably attach to the distal end of the housing. The separable distal element 38 can comprise light-blocking sides 40 and if desired a forward-facing window 42, as shown in FIG. 3E, configured to transmit at least the excitation light, the fluorescent light and the heat levels without substantial alteration. The separable distal element 38 can also comprise recesses 48, 50 to accommodate expected physical structures at a target site, to avoid a side wall from impacting an image/increase scanning/imaging field of view, etc. The distal end 6 of the housing 8 and the separable distal element 38 can be cooperatively configured such that the separable distal element 38 can be snapped on and off the distal end 6 of the housing 8. For example, the distal end 6 of the housing 8 and the separable distal element 38 can comprise cooperative projections 52 and detents 54 configured such that the separable distal element 38 can be snapped on and off the distal end 6 of the housing 8 by cooperatively engaging and releasing such elements. Image capture device 120 can further comprise a plug-port 44 and a battery bay 46.

In the embodiment depicted in FIGS. 3A-3F, the housing 8 is configured to be held in a single hand of a user, and is configured to fit within a human oral cavity and to scan at least a rear surface of such oral cavity and/or a throat behind such oral cavity.

Figure 3G:
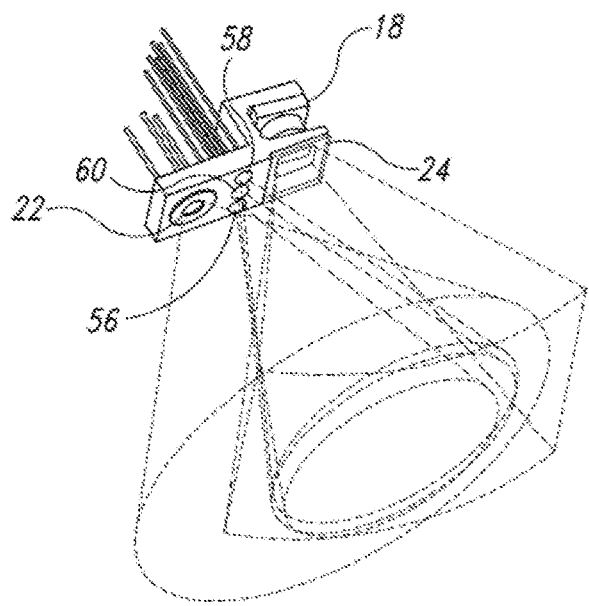
Figure 3H:
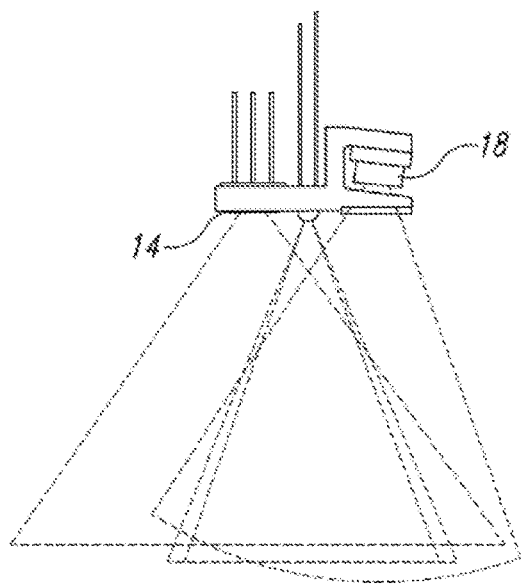

FIGS. 3G and 3H show further information about the light emitters, light sensors and heat sensors. In this embodiment, all are located at the distal end 6 of the housing 8 (not shown) and are all forward-facing and aimed to substantially cover a same area of the target site, as demonstrated by the overlapping fields of view in the figures. Also in this embodiment, excitation light emitters include red LED 56, green LED 58, and blue LED 60.

Figure 3I:
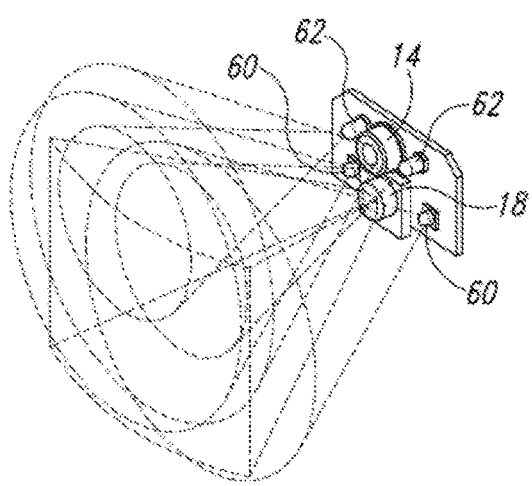

FIG. 3I shows a further embodiment concerning light emitters, light sensors and heat sensors. In this embodiment, the array includes two white light emitting LEDs 62, and two blue LEDs 60, as well as a camera 18 and a radiant heat sensor 14.

Figure 3J:
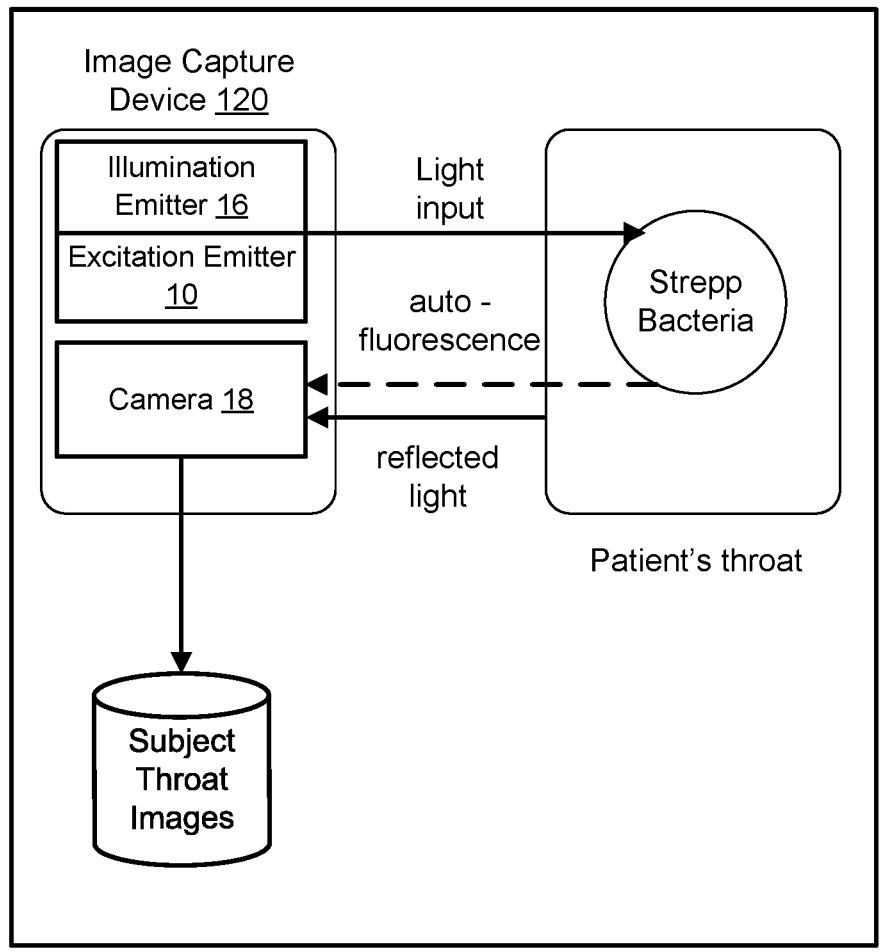
FIG. 3J is an interaction diagram for the image capture of a subject's throat, according to one embodiment.

FIG. 3J shows an interaction diagram of the image capture process for providing the set of subject throat images to the detection system 100, according to one embodiment. For white images, the illumination emitter 16 provides light input to the subject's throat, and the camera 18 simultaneously records a white image of the throat. The white image of the throat may be formed by collecting light reflected from the throat of the subject. For excitation images, also referred to herein as an "blue images," the excitation emitter 10 provides light input to the subject's throat at a specific excitation wavelength, and the camera 18 simultaneously records a blue image of the throat, according to one embodiment. The blue image may be formed by collecting light emitted from the throat of the subject as a result of auto-fluorescence, in addition to light reflected by the throat of the subject. In some cases, the light from auto-fluorescence is a different wavelength than the excitation wavelength. In one embodiment, the excitation emitter 10 provides light input to another part of the subject's body, and the camera 18 simultaneously records an excitation image of the part of the subject's body. In some embodiments, the excitation emitter 10 provides blue light input, but in other embodiments, the excitation emitter may provide light input at wavelengths corresponding to other colors. In some embodiments, the subject throat images include images other than the white images and the blue images. For example, the captured subject throat images may include images captured in multiple wavelengths and multiple lighting conditions. In embodiments where the detection system 100 targets other diseases and/or medical conditions, the captured subject images may include images other than the white images and the blue images.

In the case where targeted bacterial pathogens are present in the subject's throat, fluorescent hosts in the bacteria, for example a porphyrin, cause the bacteria to auto-fluoresce in response to the light input from the excitation emitter 10. The camera 18 will capture this auto-fluorescence as part of the blue image. In some embodiments, viruses or other factors are targeted instead of bacteria. In further embodiments, the excitation emitter 10 causes the targeted virus or other factor to fluoresce in response to the light input from the excitation emitter 10.

The white image and blue image are included in the set of subject throat images provided to the chained model 150 for use in determining a disease state prediction of the subject. In one embodiment, more than one blue image or white image may be included in the set of subject throat images. In another embodiment, images other than the blue image or white image may be included in the set of subject throat images, for example images with illumination conditions from the image capture device 120. For example, the subject throat images provided to the chained model 150 may include images captured in other colors or other wavelengths of light, according to some embodiments.

In another example, the detection system 100 may be used to detect diseases and conditions related to skin legions present on a subject. In such a case, the image capture device 120 captures white images and excitation images of the skin legions. In some embodiments, the image capture device 120 only captures white images. In other embodiments, the image capture device 120 only captures excitation images of the skin legions. The captured images are provided to the chained model 150 to determine a disease state prediction related to the skin legion.

III.B. Collection of Clinical Factors

Clinical factors for the subject are collected substantially contemporaneously with the capture of subject throat images by the image capture device 120. In one embodiment, the clinical factors for a subject are collected by the medical professional 112 and submitted to the chained model 150 using the client device 111. In another embodiment, the clinical factors are provided by a subject without the aid of or without interacting with the medical professional 112. For example, the subject may report the clinical factors through an application on a client device 110, such as a smartphone. In alternate embodiments, one or more of the clinical factors are not collected contemporaneously to the capture of images by the image capture device 120. For example, if age is a clinical factor for predicting a presence of a disease, the age of the subject may be recorded at a different time than the image capture.

III.C. Image Capture and Preprocessing

For the case of diagnosing a pharyngitis case related to the presence of Streptococci bacteria, the colored light spectra emitted by porphyrins resulting from Streptococci bacteria metabolism in the oral cavity is filtered by specific wavelength. It is then captured by the image capture device's camera 18 as white light and blue light digital images. These images are then curated, centered and cropped by an image pre-processing algorithm that assess the quality and suitability of these images for use in the image model.

Good image pre-processing leads to a robust AI model for accurate predictions. Pre-Processing techniques that may be performed on the set of subject throat images may include: uniform aspect ratio, rescaling, normalization, segmentation, cropping, object detection, dimensionality deduction/increment, brightness adjustment, data augmentation techniques to increase the data size like: Image Shifting, flipping, zoom in/out, rotation etc., determining quality of the image to exclude bad images from being a part of training dataset, image pixel correction, and performing a FV image florescence brightness algorithm.

IV. Chained Model

IV.A. Image Model Training

In one embodiment, the chained model 150 includes an image model 400 and a classifier 500. The training of the image model 400 and classifier 500 will be discussed below.

FIG. 4 illustrates a process for training of an image model 400 within a chained model 150, according to one embodiment. The image model 400 is trained on a first set of training throat images associated with a first set of training subjects and a corresponding first set of training labels. In one embodiment, the training images are of sore throats captured under fluorescent light, white light, and ambient light. The fluorescent light may contain blue light at a wavelength for fluorescing porphyrins associated with streptococcal bacteria.

Each training subject has one of several pre-determined labels. In one embodiment, the pre-determined labels distinguishes the subject as having A) a bacterial pathogen, B) a viral pathogen, or C) an absence of a pathogen. The label may be a categorical label (e.g., A, B, C), or it may be a numerical label (e.g., −1, 0, 1). The first set of training throat images and the associated labels are provided by a training database 415. The first set of training throat images may be captured by the image capture device 120. The labels for the first set of training subjects is provided on the basis that disease states of the first set of training subjects are previously known, for example as determined by traditional cell culturing and evaluation by one or more medical professionals evaluating the training set of subjects.

The image model 400 is trained by determining image parameter coefficients 430, each associated with a corresponding image parameter, (not shown). Collectively, the image parameter coefficients 430 are determined so as to best represent the relationship between the first set of training subject throat images input into a function of the image model 400 and their associated labels. Generally, the image model 400 is a supervised machine learning technique. In one embodiment, the image model 400 is a convolutional neural network model. In a further embodiment, the convolutional neural network is trained using transfer learning with fine tuning. In other embodiments, the image model 400 is specifically a VGG neural network, a ResNet neural network, or an Inception V4 neural network. In other embodiments, other types of machine learning models and training methods may be used, examples of which include but are not limited to: stochastic gradient descent, transfer learning algorithms, learning rate annealing, cyclic learning rates, differential learning rates, regularization techniques such as batch normalization, ensembling neural networks, etc.

Once the parameter coefficients are known, the image model 400 may be used for prediction, as discussed in FIG. 5 and FIG. 6 by accessing the image parameter coefficients 430 and the function specified by the model, and inputting input values for the image parameters to generate a prediction of pathogen presence. The prediction generated for a subject by the image model 400 may include one or more of: a probability of a presence of a bacterial pathogen, a probability of a presence of a viral pathogen, and a probability of an absence of a pathogen. The prediction may be output in the form of a vector including one or more of the above numerical values. The prediction may also output a separate numerical confidence in the prediction.

In one embodiment, the prediction may include one or more of: a probability of a presence of exudate, a probability of a presence of petechiae, a probability of a presence of swollen tonsils, and a probability of a presence of a swollen uvula. In this embodiment, the image model 400 is training with training images and corresponding training labels indicating the presence or absence of these conditions. Again, the prediction may be output in the form of a vector including one or more of the above numerical values, and the prediction may also output a separate numerical confidence in the prediction. In some embodiments, where the detection system 100 is used for diseases and/or medical conditions other than pharyngitis, the prediction may include one or more of: a presence of plaque, a presence of oral mucosa, a presence of cancer, gastroesophageal reflux disease (GERD) detection, and a presence of bacterial pathogens (e.g, *e.coli*, salmonella, and other pathogens).

In other embodiments, the image model 400 is any machine learning model that directly or indirectly generates a prediction of a presence of a disease factor such as a pathogen, a presence of or property of a tumor, or a degree of swelling of a body part. In one embodiment, the image model 400 is a machine learning model that performs feature detection on images (e.g., white images, blue images, or images in other wavelengths or lighting conditions) of a subject's throat, as well as color classification. According to some embodiments the feature detection and color classification may be used to determine targeted feature metrics including, but not limited to: presence/size/shape/location of the oral cavity, oral cavity symmetry, presence/size/shape/location tonsils, tonsil redness, tonsil swelling, a soft or hard palate, presence of red spots on the palate, streaks of pus, white patches, and dry mouth. Each of the feature metrics may correspond to an identified feature in an image. For example, a feature metric may indicate a presence of an identified feature or a property of an identified feature. In some embodiments, feature detection on the white images may complement the feature detection performed on the blue images.

In some embodiments, for the blue images, the feature detection and the color classification determines targeted infection metrics including, but not limited to: presence/size/shape/location of an infected area, an intensity, and a pattern identification. In some embodiments the feature detection and the color classification is used for images other than the blue images. In some embodiments, one or more of the targeted infection metrics generated by the image model for the blue images indicate characteristics of auto-fluorescence in one or more regions of a subject's throat captured in the blue image, in response to illumination from an excitation light source (e.g., blue light from the image capture device). Each of the infection metrics may correspond to an infection in the subject. For example, an infection metric may indicate a presence of a certain infection (e.g., a viral infection or a bacterial infection) in the subject or a property of an infection. In one embodiment the determined feature metrics and infection metrics may then be provided independently of or alongside the prediction of a presence of a pathogen according to the methods described above to the classifier as inputs for generating a patient's disease state prediction. In other embodiments, the determined feature metrics and infection metrics may be provided without the prediction of a presence of a pathogen to the classifier as inputs for generating a patient's disease state. In one embodiment, feature detection and color classification is performed using k-means clustering, however other unsupervised machine learning techniques may also be used.

IV.B. Classifier Training

FIG. 5 illustrates a process for training of a classifier within a chained model 150, according to one embodiment. The classifier 500 is trained using a set of training predictions of pathogen presence generated by the pre-trained image model 400 based on a second set of training throat images, training clinical factors associated with a second set of training subjects, and a corresponding second training set of labels. In one embodiment, the classifier 500 is trained using feature metrics and infection metrics generated by the pre-trained image model 400 based on the second set of training throat images, in addition to or independently of the training data described above. As with the first set of training labels, each subject from the second set of training subjects has a corresponding pre-determined label distinguishing the subject as having a bacterial pathogen, a viral pathogen, or an absence of a pathogen. Again, these labels may be determined by traditional cell culturing and evaluation by one or more medical professionals evaluating the training set of subjects. The labels may alternatively be determined by other methods.

Again, the second set of training subject throat images and the associated labels are provided by the training database 415. The training clinical factors are provided by a training clinical database 515. The training clinical database 515 contains clinical factors for each of the second set of training subjects collected by a medical professional or device 120. These images are generally collected substantially simultaneously with the capture of the corresponding training subject throat images for that subject.

The classifier 500 is trained by determining classifier parameter coefficients 530, each associated with each classifier parameter (not shown). The coefficients are trained so as to collectively best represent the relationship between the input values (predictions of pathogen presence and clinical factors) of the second set of training subjects and a function of the classifier to the second set of training labels.

Generally, the classifier 500 is trained using a supervised machine learning technique. In one embodiment, the classifier 500 is a neural network model, trained using trained using stochastic gradient descent. In other embodiments, other types of classifiers and training methods may be used, examples of which include but are not limited to linear, logistic, and other forms of regression (e.g., elastic net, multinomial regression), decision trees (e.g., random forest, gradient boosting), support vector machines, classifiers (e.g. Naïve Bayes classifier), fuzzy matching. In other embodiments, the classifier may perform classical statistical analysis methods that include, but are not limited to: correlations, hypothesis tests, and analysis of variance (ANOVA).

Once the parameter coefficients are known, the classifier model 500 may be used for prediction, as discussed in FIG. 6 by accessing the classifier parameter coefficients 530 and the function specified by the classifier, and inputting input values for the parameters to generate a prediction of disease state. The disease state prediction of the subject generated by the classifier 500 may include one or more of: a probability of bacterial infection, a probability of viral infection, and a probability of no infection. Additionally or alternatively, the disease state prediction may include probabilities indicating the presence of anatomical morphologies or symptoms. In one embodiment, the probabilities indicating the presence of anatomical morphologies or systems include one or more of: a probability of a presence of exudate, a probability of a presence of petechiae, a probability of a presence of swollen tonsils, and a probability of a presence of a swollen uvula. In cases where diseases or conditions other than pharyngitis are targeted, the disease state predictions may indicate probabilities of other morphologies or symptoms.

IV.C. Clinical Factors

In one embodiment, the set of clinical factors of the subject used by the classifier 500 in the chained model 150 may include, but are not limited to: an age, a presence or absence of swollen lymph nodes, a subject temperature, a presence or absence of a fever, a presence or absence of coughing symptoms, a presence or absence of a runny nose, a presence or absence of a headache, a presence or absence of body aches, a presence or absence of vomiting, a presence or absence of diarrhea, a presence or absence of fatigue, a presence or absence of chills, a duration of pharyngitis, and a set of symptoms correlated with the Centor procedure.

V. Model Inference

FIG. 6 illustrates a process for generating disease state predictions using a chained model 150, according to one embodiment. The chained model 150 receives as input a set of subject throat images from a subject and a set of clinical factors collected by a medical professional 112 substantially contemporaneously to the capture of the set of subject throat images. In one embodiment, the images of the subject are of sore throats captured under fluorescent light, white light, and ambient light. The chained model 150 generates disease state prediction for the subject. In some embodiments, the input set of subject throat images may include only white images captured with white lighting conditions or ambient lighting conditions, or only blue images captured using illumination from an excitation light source for fluorescence. In other embodiments, the input set of subject throat images may include subject throat images captured under other lighting conditions. For example, the input set of subject throat images may include multiple images capturing multiple wavelengths of light.

The generation of the disease state prediction for the subject is a two-step process. A first step includes inputting the set of subject throat images to the image model 400. The image model 400 accesses the image parameter coefficients 430 and generates a pathogen presence prediction for the subject. The pathogen presence prediction is provided together with the set of clinical factors as inputs to the classifier 500. The classifier 500 accesses the classifier parameter coefficients 530 and together with clinical factors and pathogen presence prediction generates a disease state prediction for the subject. The disease state prediction may then be provided to the client device 110 and displayed to a medical professional or the subject.

In one embodiment, the chained model 150 can provide a disease state prediction solely using the pathogen presence prediction without accessing the clinical factors for the subject. In this case, the set of subject throat images is sufficient for determining the disease state prediction, and only the output of the image model 400 is used.

In some embodiments, the image model 400 is trained using blue images, white images, images captured in a different wavelength of light or different lighting conditions, or some combination thereof, but when generating disease state predictions, the chained model 150 may have input subject throat images that are captured in a different wavelength of light or different lighting conditions than the training images. For example, the image model 400 may be trained using a combination of white images and blue images, but only white images may be used as inputs for the chained model 150 when generating disease state predictions for a subject.

Figure 7:
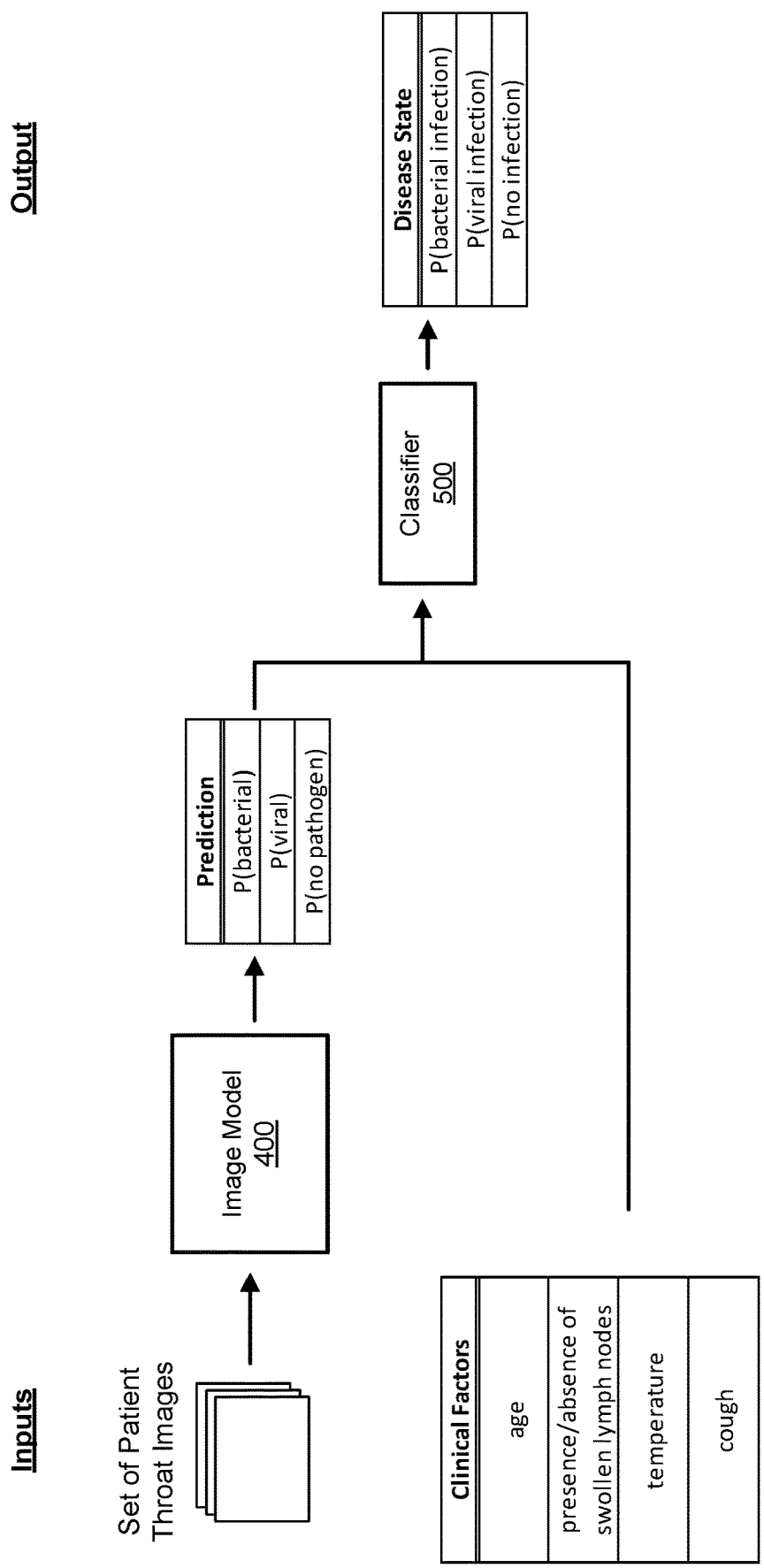
FIG. 7 illustrates example input and output vectors relevant to the chained model, according to one embodiment.

FIG. 7 illustrates example input and output vectors relevant to the chained model 150, according to one embodiment. The input vectors include the set of subject throat images and the clinical factors. The resulting output vector of the chained model is a disease state prediction, which includes probabilities for various types of infections in the subject.

In the example, shown in FIG. 7, the clinical factors include age, a presence or absence of swollen lymph nodes, a body temperature, and a presence or absence of a cough. The set of subject throat images includes white images and blue images of the subject's throat captured with the image capture device 120. The disease state prediction includes a probability of a bacterial infection, a probability of a viral infection, and a probability of no infection, as determined by the chained model 150, based on the input vectors. The input vectors and resulting output vectors of the chained model 150 may be different than what is shown in FIG. 7. For example, if a disease or condition other than pharyngitis is targeted, the input vectors and resulting output vectors may be relevant to the targeted disease.

Figure 8:
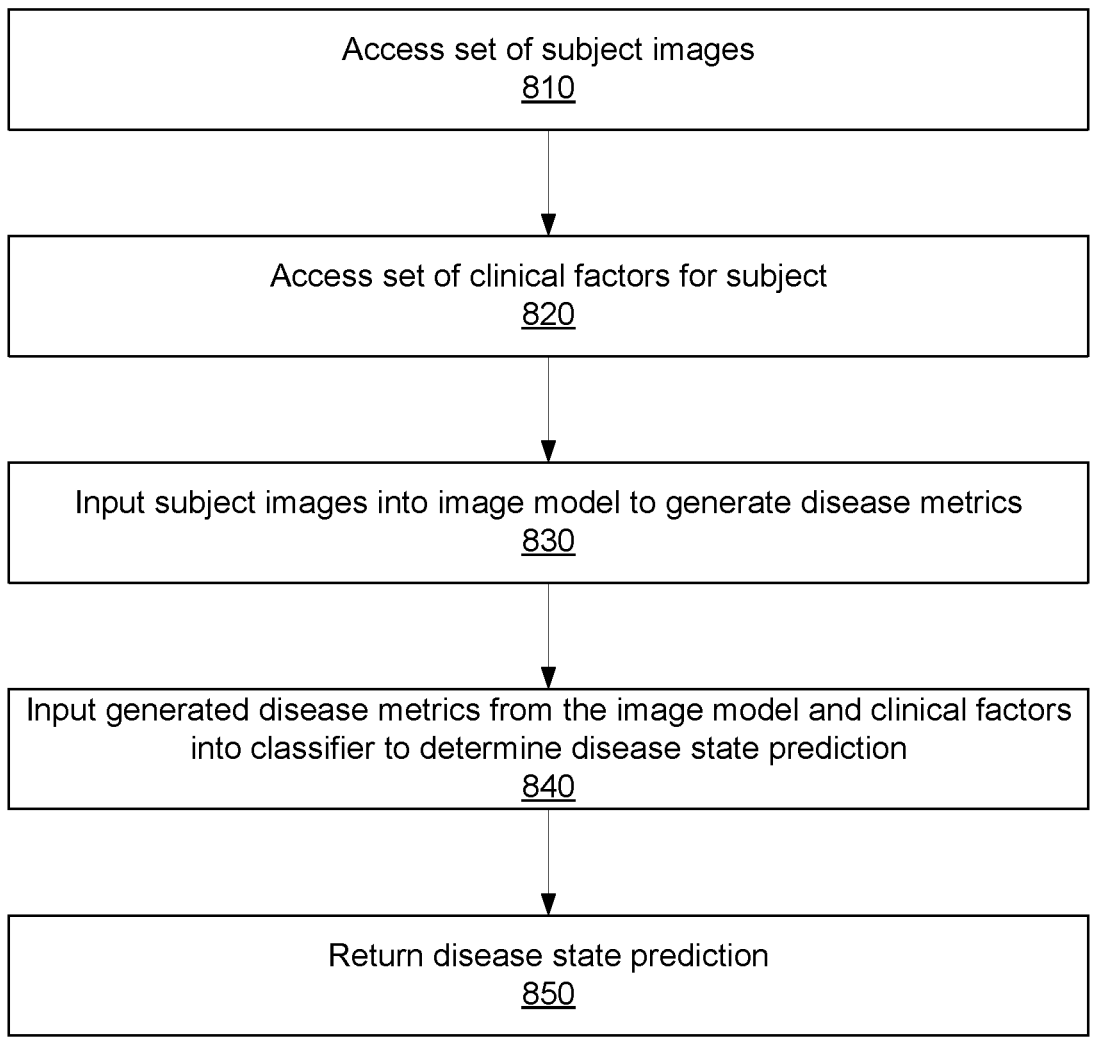
FIG. 8 is a flowchart of returning a disease state prediction for subject determined by a chained model, according to one embodiment The figures depict various embodiments of the presented invention for purposes of illustration only. One skilled in the art will readily recognize from the following discussion that alternative embodiments of the structures and methods illustrated herein may be employed without departing from the principles described herein.

FIG. 8 is a flowchart 800 of returning a disease state prediction for subject determined by a chained model 150, according to one embodiment. The disease state prediction indicates a probability of a subject having a disease or medical condition, according to some embodiments. The chained model 150 accesses 810 a set of subject images associated with the subject. The subject images depict a part of the subject's body. For example, the subject image may be an image of the subject's throat. The chained model 150 accesses 820 a set of clinical factors for the subject. The clinical factors are recorded substantially contemporaneously with the capture of the subject images. The subject images are inputted 830 into the image model 400 to generate disease metrics. The generated disease metrics and the clinical factors are then inputted into the classifier 500 to determine the disease state prediction for the subject, and the determined disease state prediction is returned 850.

VI. Benefits

The detection system described herein provides for dry in-situ clinical prediction of the presence/absence of bacterial and viral pathogen infections without the need for any pathological or laboratory tests. The detection system, according to some embodiments, may provide subjects with a home diagnostic tool for strep throat. This may effectively reduce the financial burden of treating pharyngitis for both healthcare providers and subjects, as well as reduce the time necessary to determine an accurate diagnosis. Additionally, the detection system may provide accurate predictions for diseases and conditions other than strep throat.

VII. Additional Considerations

Although the discussion above includes examples focusing on pharyngitis and strep throat specifically, all systems and processes described herein are equally applicable to other conditions.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope of the ideas described herein.

What is claimed is:

1. A method comprising:
   accessing a set of subject throat images from a subject capturing an inside of the subject's throat;
   accessing a set of clinical factors from the subject, the clinical factors collected by a device or a medical practitioner substantially contemporaneously with the capture of the subject throat images;
   inputting the subject throat images into an image model to generate a pathogen presence prediction for the subject, wherein the image model was trained in part using training throat images that include various bacterial pathogens, and the pathogen presence prediction describes in part whether any of the various bacterial pathogens are present in the subject;
   inputting the pathogen presence prediction and the clinical factors into a classifier to determine a disease state prediction; and
   returning the disease state prediction.

2. The method of claim 1, wherein the image model comprises:
   a set of image parameter coefficients trained using a first set of training throat images and a first set of training labels, each corresponding to a first set of training subjects, the first set of training labels comprising:
      a viral label indicating a presence of a viral pathogen,
      a bacterial label indicating a presence of a bacterial pathogen, and
      a clear label indicating an absence of pathogens; and
   a function relating one of the throat images and the image parameter coefficients to the pathogen presence prediction.

3. The method of claim 1, wherein the classifier comprises:
   a set of classifier parameter coefficients trained using a set of training pathogen presence predictions, a set of training clinical factors, and a second set of training labels, each corresponding to a second set of training subjects,
      the second set of training labels comprising:
         a viral label indicating a presence of a viral pathogen,
         a bacterial label indicating a presence of a bacterial pathogen, and
         a clear subset indicating an absence of pathogens,
      the set of training pathogen presence predictions generated by inputting a second set of training throat images corresponding to the second set of subjects into the image model;

the set of training clinical factors collected by a device or a medical practitioner substantially contemporaneously with the capture of the second set of training throat images, and a function relating the pathogen presence predictions, the clinical factors, and the classifier parameter coefficients to the disease state prediction.

4. The method of claim 1, wherein the set of training throat images were captured using the same image capture device used to capture the set of subject throat images.

5. The method of claim 4, wherein the set of training throat images and the set of subject throat images each comprise
a plurality of throat images captured under ambient light conditions,
a plurality of throat images captured under fluorescent light, and
a plurality of throat images captured under white light illumination.

6. The method of claim 1, wherein the set of subject throat images is recorded with an image capture device comprising:
a housing;
a light emitter configured to emit excitation light at a wavelength selected to elicit auto-fluorescence of a pathogen;
a light sensor configured to detect light emissions or an absence of light emissions resulting from the auto-fluorescence of the pathogen; and
a display.

7. The method of claim 6, wherein the disease state prediction is displayed on the display of the image capture device.

8. The method of claim 1, wherein the set of subject throat images is recorded by a mobile phone device.

9. The method of claim 8, wherein the disease state prediction is displayed on the mobile phone device.

10. The method of claim 1, wherein the set of subject throat images comprises
at least one blue throat image captured using a blue light emitter; and
and at least one white throat image captured using a white light emitter.

11. The method of claim 1, wherein the subject throat images captures data regarding multiple wavelengths of light.

12. The method of claim 1, wherein at least one of the subject throat images captures infrared light image data.

13. The method of claim 1, wherein the set of subject throat images are pre-processed before being input into the image model, the pre-processing comprising at least one from the group consisting of:
uniform aspect ratio correction,
rescaling,
normalization,
object detection,
segmentation,
cropping,
dimensionality reduction,
dimensionality increment,
brightness adjustment,
image shifting,
image flipping,
zoom in or out,
image rotation,
image quality filtering, and
image pixel correction.

14. The method of claim 1, wherein the image model is a convolutional neural network (CNN).

15. The method of claim 1, wherein the classifier is trained using one of: linear regression, logistic regression, multinomial regression, elastic net regression.

16. The method of claim 1, wherein the classifier is one of a random forest classifier, a gradient boosted classifier, a support vector machine classifier, and a Naïve Bayes classifier.

17. The method of claim 1, wherein the pathogen presence prediction comprises at least one of:
a probability of a presence of a viral pathogen,
a probability of a presence of a bacterial pathogen, and
a probability of an absence of a pathogen.

18. The method of claim 1, wherein the pathogen presence prediction comprises at least one of:
a probability of a presence of exudate,
a probability of a presence of petechiae,
a probability of a presence of swollen tonsils, and
a probability of a presence of a swollen uvula.

19. The method of claim 1, the disease state prediction comprises at least one of:
a probability of viral pathogen infection,
a probability of bacterial pathogen infection, and
a probability of no pathogen infection.

20. The method of claim 1, wherein the set of clinical factors comprises at least one from the group consisting of:
age,
a presence or absence of swollen lymph nodes,
subject temperature,
a presence or absence of a fever, and
a presence or absence of a cough.

21. The method of claim 1, wherein the set of clinical factors comprises at least one from the group consisting of:
age,
a presence or absence of swollen lymph nodes,
subject temperature,
a presence or absence of fever
a presence or absence of a cough,
a presence or absence of a runny nose,
a presence or absence of a headache,
a presence or absence of body aches,
a presence or absence of vomiting,
a presence or absence of diarrhea,
a presence or absence of fatigue,
a presence or absence of chills, and
a duration of pharyngitis.

22. A computer system comprising a computer processor and a memory, the memory storing computer program instructions that when executed by the computer processor cause the processor to:
access a set of subject throat images from a subject;
access a set of clinical factors from the subject, the clinical factors collected by a device or a medical practitioner substantially contemporaneously with the capture of the subject throat images;
input the subject throat images into an image model to generate a pathogen presence prediction for the subject, wherein the image model was trained in part using training throat images that include various bacterial pathogens, and the pathogen presence prediction describes in part whether any of the various bacterial pathogens are present in the subject;
input the pathogen presence prediction and the clinical factors into a classifier to determine a disease state prediction; and
return the disease state prediction.

23. A non-transitory computer readable storage medium comprising computer program instructions that when executed by a computer processor cause the processor to:
    access a set of subject throat images from a subject;
    access a set of clinical factors from the subject, the clinical factors collected by a device or a medical practitioner substantially contemporaneously with the capture of the subject throat images;
    input the subject throat images into an image model to generate a pathogen presence prediction for the subject, wherein the image model was trained in part using training throat images that include various bacterial pathogens, and the pathogen presence prediction describes in part whether any of the various bacterial pathogens are present in the subject;
    input the pathogen presence prediction and the clinical factors into a classifier to determine a disease state prediction; and
    return the disease state prediction.

24. A method comprising:
    accessing a set of subject images, the subject images capturing a part of a subject's body;
    accessing a set of clinical factors from the subject, the clinical factors collected by a device or a medical practitioner substantially contemporaneously with the capture of the subject images;
    inputting the subject images into an image model to generate disease metrics for disease prediction for the subject, wherein the image model was trained in part using training throat images that include various bacterial pathogens, and the disease metrics describe in part whether any of the various bacterial pathogens are present in the subject;
    inputting the disease metrics and the clinical factors into a classifier to determine a disease state prediction, the disease state prediction relating to a disease or medical condition; and
    returning the disease state prediction.

25. The method of claim 24, wherein the disease metrics comprise:
    feature metrics corresponding to identified features in the subject image, and infection metrics corresponding to a presence of a bacterial or viral infection in the part of the subject's body.

26. The method of claim 24, wherein the image model comprises:
    a set of image parameter coefficients trained using a first set of training subject images and a first set of training labels, each corresponding to a first set of training subjects, the first set of training labels comprising:
        a viral label indicating a presence of a viral pathogen,
        a bacterial label indicating a presence of a bacterial pathogen, and
        a clear label indicating an absence of pathogens; and
    a function relating one of the subject images and the image parameter coefficients to the disease metrics.

27. The method of claim 24, wherein the classifier comprises:
    a set of classifier parameter coefficients trained using a set of training disease metrics, a set of training clinical factors, and a second set of training labels, each corresponding to a second set of training subjects,
        the second set of training labels comprising:
            a viral label indicating a presence of a viral pathogen,
            a bacterial label indicating a presence of a bacterial pathogen, and
            a clear subset indicating an absence of pathogens,
        the set of training disease metrics generated by inputting a second set of training subject images corresponding to the second set of subjects into the image model;
        the set of training clinical factors collected by a device or a medical practitioner substantially contemporaneously with the capture of the second set of training subject images, and
    a function relating the disease metrics, the clinical factors, and the classifier parameter coefficients to the disease state prediction.

* * * * *